US006522920B2

(12) United States Patent
Silvian et al.

(10) Patent No.: US 6,522,920 B2
(45) Date of Patent: Feb. 18, 2003

(54) SYSTEM AND METHOD OF PROTECTING TRANSFORMER-DRIVEN SWITCHES FROM EXTERNAL MAGNETIC FIELDS

(75) Inventors: Sergiu Silvian, La Crescenta, CA (US); Wayne A. Morgan, Northridge, CA (US)

(73) Assignee: Pacesetter, Inc., Sylmar, CA (US)

( * ) Notice: Subject to any disclaimer, the term of this patent is extended or adjusted under 35 U.S.C. 154(b) by 252 days.

(21) Appl. No.: 09/735,168

(22) Filed: Dec. 11, 2000

(65) Prior Publication Data

US 2002/0072769 A1 Jun. 13, 2002

(51) Int. Cl.[7] .............................................. A61N 1/08
(52) U.S. Cl. .............................. 607/2; 607/4; 607/30; 607/32
(58) Field of Search .............................. 607/2, 4, 5, 7, 607/9, 12, 30, 32, 33, 60, 72, 74

(56) References Cited

U.S. PATENT DOCUMENTS

| 4,361,153 A | * 11/1982 | Slocum et al. ................. 607/32 |
| 4,800,883 A | 1/1989 | Winstrom ...................... 607/7 |
| 5,285,779 A | 2/1994 | Cameron et al. ............... 607/5 |
| 5,318,591 A | 6/1994 | Causey, III et al. ............ 607/5 |
| 5,609,618 A | 3/1997 | Archer ......................... 607/74 |
| 5,649,971 A | 7/1997 | Fain et al. .................... 607/72 |
| 5,658,319 A | 8/1997 | Kroll ............................ 607/7 |
| 5,745,350 A | 4/1998 | Archer et al. ................. 363/15 |
| 5,766,226 A | 6/1998 | Pedersen ...................... 607/5 |
| 5,913,877 A | 6/1999 | Kroll et al. ................... 607/5 |
| 6,101,417 A | * 8/2000 | Vogel et al. .................. 607/30 |

\* cited by examiner

*Primary Examiner*—Willis R. Wolfe

(57) ABSTRACT

A protection device for use in an implantable medical device such as an ICD that communicates with an external programmer. The protection device includes one or more control blocks that inhibit gate triggers for the switching elements (IGBTs) of an H-bridge whenever the drive voltage for these switching elements falls below a pre-determined level. Each control block provides a controlled path to charge the IGBT gate when triggering is required and, importantly, when the gate drive voltage is above a predetermined threshold. The control block further prevents inadvertent or spurious triggering and protects the gate circuitry of the switching elements by providing a low impedance path between the gates and sources of the IGBTs when the latter switching elements are intended to be turned OFF. Additionally, the control blocks protect the IGBTs from over-voltage effects by clamping the output of the gate trigger with a shunt regulator circuit.

23 Claims, 7 Drawing Sheets

SYSTEM AND METHOD OF PROTECTING TRANSFORMER-DRIVEN SWITCHES FROM EXTERNAL MAGNETIC FIELDS

FIELD OF THE INVENTION

The present invention generally relates to implantable cardiac stimulation systems and other types of implantable medical devices. Particularly, this invention relates to a method of protecting implanted devices from the effects of external magnetic fields associated with external diagnostic/programmer systems that could result in damage to the implanted devices. More specifically, the present invention relates to an integrated circuit coupled to a high frequency carrier transformer in which the functionality of the integrated circuit prevents damage to the switches in the implanted devices by blocking driving levels with insufficient amplitude. Furthermore, with the inclusion of additional logic circuitry within the integrated circuit, the invention can control more than one protected output using only one transformer, thus contributing to a reduction in the device size.

BACKGROUND OF THE INVENTION

Implantable devices are implanted in a human or animal for the purpose of performing a desired function. This function may be purely observational or experimental in nature, such as monitoring certain body functions; or it may be therapeutic or regulatory in nature, such as providing critical electrical stimulation pulses to certain body tissue, nerves or organs for the purpose of causing a desired response. Implantable medical devices such as pacemakers, perform both observational and regulatory functions, i.e., they monitor the heart to ensure it beats at appropriate intervals; and if not, they cause an electrical stimulation pulse to be delivered to the heart in an attempt to force the heart to beat at an appropriate rate. In some cases, a number of functions are required for the patient's well being. With space at a premium, it is desirable that multiple functions be incorporated into a single device.

An implantable device, such as a pacemaker, must perform its functions at minimum inconvenience and risk to the person or animal within whom it is used. It must be long-lived and reliable. In most cases, the volume must be minimized. Typically, a noninvasive telemetry system must be provided to allow data and commands to be readily transmitted between the implantable device and an external programmer. The external programmer provides a convenient mechanism through which the operation of the implantable device can be controlled and monitored, and through which data sensed or detected by the implantable device can be transferred out of the implantable device to an external (non-implanted) location where it can be read, interpreted, or otherwise used in a constructive manner.

A permanent magnet can be placed over the implantable device to enable the transmission of specific commands to the implantable device. The implanted device senses the external magnetic field using a reed switch or a special magnetic sensor.

However, the strong magnetic field associated with the external magnet might adversely affect key components in the implantable device. In particular, the strong magnetic field of the external magnet might have unintended, deleterious effects on the high frequency carrier transformer and, ultimately, on the HV (high voltage) switching elements within the device.

In an implantable cardioverter/defibrillator (ICD), key elements in the generation and application of the high voltage electrical stimulation pulses are the main electrical switches that discharge electrical energy (ranging from less than 0.5 Joules to as much as 40 Joules) into the appropriate regions of the heart. These switches, typically power MOSFETs (metal oxide semiconductor field effect transistors) or IGBTs (insulated gate bipolar transistors). If an insufficient IGBT drive voltage is applied, the IGBT can be destroyed, thus rendering the implantable device non-functional.

Drive voltages for the gates of the main switches are derived from the rectified output of the secondary of a high frequency carrier transformer. Reference is made to U.S. Pat. No. 4,800,883 to Winstrom. The use of a 2 MHz carrier frequency allows the core of the transformer to be substantially reduced in size, as required by the constraints on the volume of the implantable device.

However, the reduction in the size of the core leaves the implantable device susceptible to the effects of external magnetic fields such as those represented by an external magnet. In particular, if the core is subjected to a magnetic field of sufficient magnitude and/or asymmetry, the volt-second product of the core may be exceeded. As a result, the core saturates and the output of the secondary decreases due to the reduced coupling factor between the primary and secondary windings. This reduced secondary voltage may be insufficient to effectively and safely drive the gates of the MOSFETs/IGBTs, and might result in damage to or destruction of these switching elements.

Ideally, the isolation transformer is not used while the external magnet is present and, as such, implantable devices are typically equipped with a magnetic field sensor such as a reed switch or Hall effect device that inhibits triggers to the main switching elements. However, it is possible that the magnetic sensor in the implantable device may not sense the field because of dead zones or field nulls near the sensor. For example, even a strong magnetic field perpendicular to the reed switch would not actuate the latter.

If the implantable device attempts to turn on the MOSFETs/IGBTs, and if the transformer supplying the drive to the gate of the switches is saturated, the voltage at the secondary of the transformer may be below the required value, and the main switches may be damaged or destroyed. An IGBT typically requires 15V between the emitter and the gate to be fully ON. While fully on, and at a delivery current of 16 A (e.g. 800V at a 50-Ohm body impedance), the IGBT voltage drop (collector to emitter) is approximately 2V. In this case, for the duration of the applied shock of approximately 5 ms, the IGBT needs to sustain 32 W (e.g. 2V*16A). Considering that the IGBT is insufficiently driven such that the voltage drop is 40V. The current in the circuit would then be (800–40)V/50 Ohm=15.2A. The new power dissipation will be 40V*15.2A=608W, which will destroy the IGBT.

There is therefore a still unsatisfied need for a system that protects the implantable device from an external magnetic field that might saturate a transformer core and lead to damage or destruction of MOSFET/IGBT main switches therein.

SUMMARY OF THE INVENTION

The protection system of the present invention addresses and satisfies this need. The protection system includes one or more control blocks that inhibit gate triggers for the switching elements (IGBTs) of an H-bridge whenever the drive voltage for these switching elements falls below a predetermined level. Each control block provides a controlled path to charge the IGBT gate when triggering is required and, importantly, when the gate drive voltage is above a predetermined threshold.

According to a preferred embodiment, gate triggers for the MOSFETs/IGBTs are inhibited whenever the drive voltage for the MOSFETs/IGBTs falls below a pre-determined level. This reduced voltage may be due to insufficient secondary voltage resulting from a saturated transformer core or from insufficient primary voltage or even defective components. With the inclusion of readily added logic circuitry, the functionality of the invention can be extended to control more than one output that needs to be controlled at the same isolated voltage.

The foregoing and other features of the present invention are achieved by implementing a protection system that employs one or more control blocks in conjunction with a high frequency carrier transformer. The control block, in its most basic implementation, contains logic and control circuitry that inhibits low voltage gate drive pulses that could result in damage to or destruction of the MOSFETs/IGBTs in an implantable device. The control block prevents inadvertent or spurious triggering and protects the gate circuitry of the MOSFETs/IGBTs by providing a low impedance path between the gate and source of the MOSFETs/IGBTs when the devices are intended to be turned off. Additionally, it protects the MOSFETs/IGBTs from over-voltage effects by clamping the output of the gate trigger with a shunt regulator circuit.

The control block is readily produced in a typical 2 □m N-well CMOS process. This technology also includes bipolar transistors, isolated vertical npn transistors and substrate vertical pnp transistors.

Briefly, the operation of the circuit may be summarized as follows: A pulse-code modulated 2 MHz square wave is applied to the primary of a high frequency isolation transformer. The transformer is equipped with a magnetic core to enhance the primary-to-secondary coupling. The output of the secondary is half-wave rectified and is used to pulse-charge a capacitor. During the initial application of the square wave to the transformer primary, the logic circuitry, powered by a voltage derived from rectified secondary output, goes through a transient reset operation to ensure that all logic values are in well-defined states.

At this point, the embedded threshold detector determines whether the available voltage is sufficient for MOSFET/IGBT to be turned ON. In the case where the voltage exceeds the threshold level, a level signal is stored when a brief carrier interruption occurs. After the short interruption, the transformer is again energized and the IGBT is turned ON, only if signal level signal exceeds the threshold. After the IGBT is turned ON, it remains ON as long as the 2 MHz carrier is applied. When this carrier is interrupted, the circuit using three transistors that are configured as a triple Darlington (also referred to as a quick discharge circuit), are triggered, quickly discharging the IGBT gate to emitter capacitance. In addition, the circuit provides a low impedance path between the gate and source of the MOSFET/IGBT. This low impedance effectively renders the MOSFETs/IGBTs untriggerable, and protects them from inadvertent triggers and/or high voltage transients.

The protection system also includes an over-voltage protection scheme that clamps the charge voltage by means of a shunt regulator circuit.

Yet another feature of the invention is its ability to readily accommodate additional output capabilities. For example, an output, not reliant on the interrupted carrier sequence described above, could be available anytime the carrier frequency is applied. An identified use for such an output would be a means of discharging the high voltage capacitors (known as a DUMP function) of a defibrillator included in the pacemaker. Thus, a single transformer is capable of controlling both the shock and dump functions of the implantable device. The flexibility of the invention still allows a magnetic field sensor, such as a reed switch or Hall-effect probe, to be incorporated in the implanted device.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, in which:

DETAILED DESCRIPTION OF THE INVENTION

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
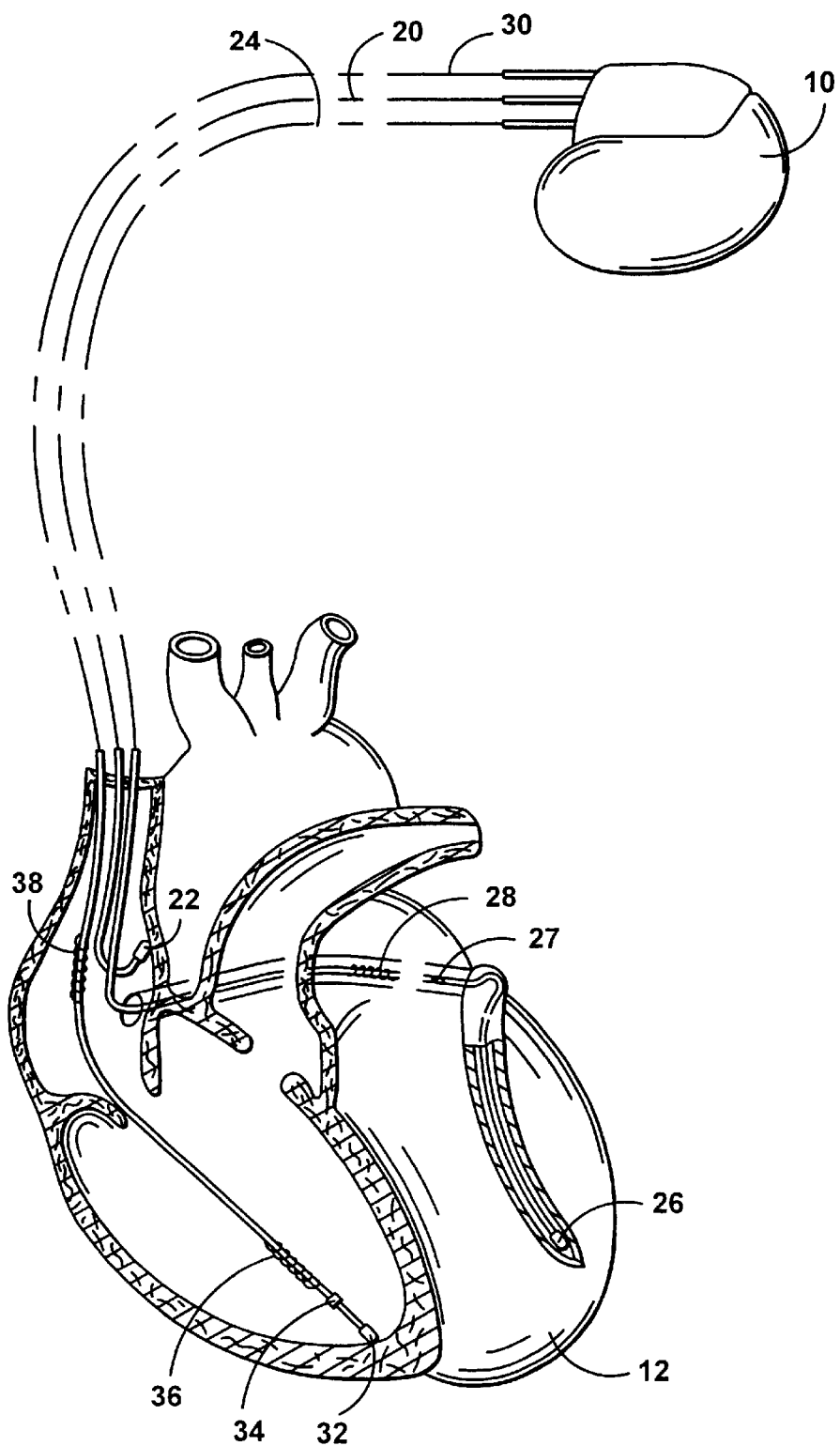
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
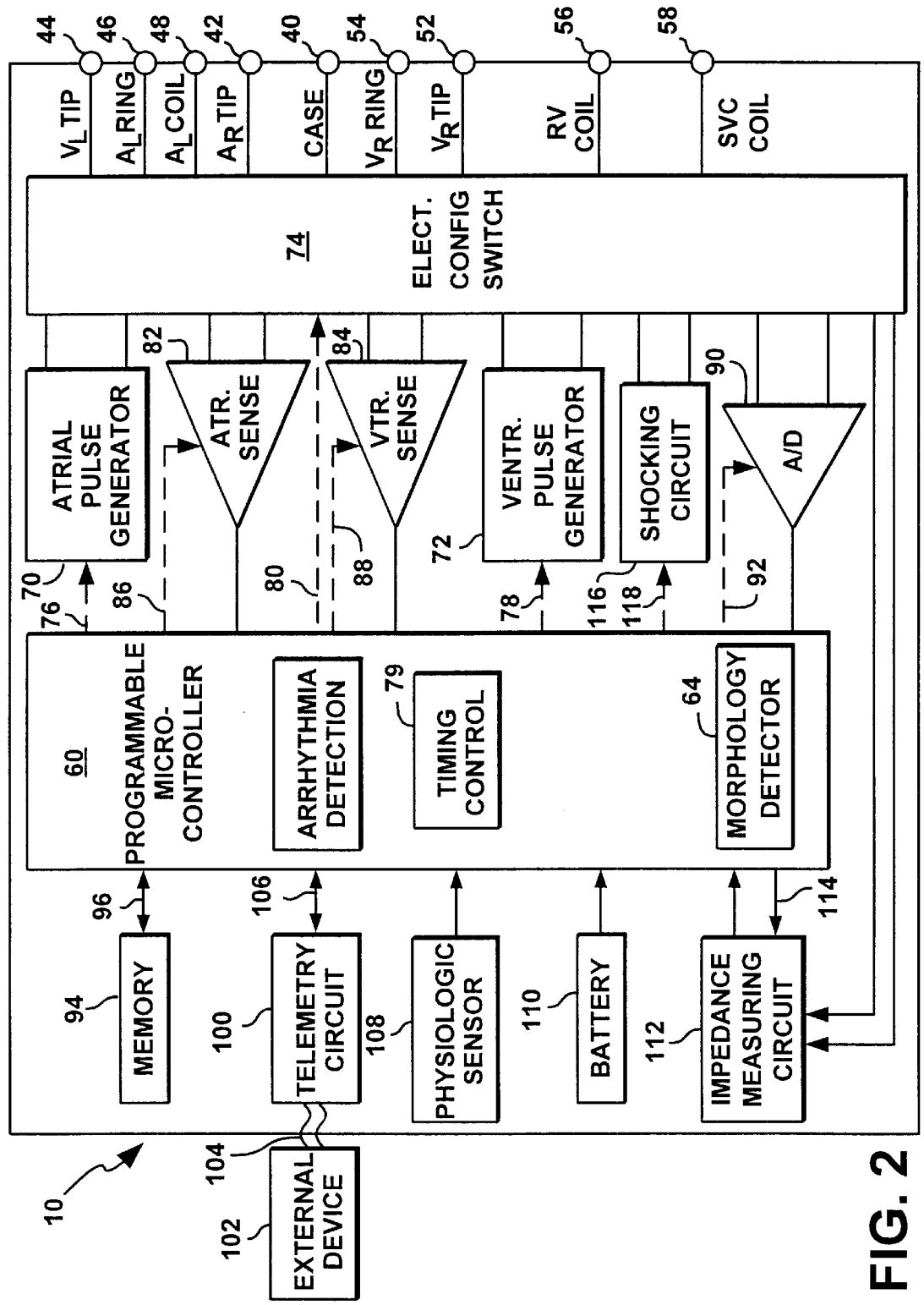
FIG. 2 is a functional block diagram of the multi-chamber implantable stimulation device of FIG. 1, illustrating the basic elements that provide cardioversion, defibrillation and/or pacing stimulation in four chambers of the heart, shown in telemetry communication with an external device/programmer.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial ($A_R$) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial tip electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart.

Cardiac signals are applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes. Advantageously, the data acquisition system 90 may be coupled to the microcontroller 60 or another detection circuitry, for detecting an evoked response from the heart 12 in response to an applied stimulus, thereby aiding in the detection of "capture".

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

The stimulation device 10 further includes a magnet detection circuitry (not shown), coupled to the microcontroller 60. The purpose of the magnet detection circuitry is to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 by a control signal 114. The impedance measuring circuit 112 is advantageously coupled to the switch bank 74 so that any desired electrode may be used.

It is a primary function of the stimulation device 10 to operate as an implantable cardioverter/defibrillator (ICD) device. That is, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
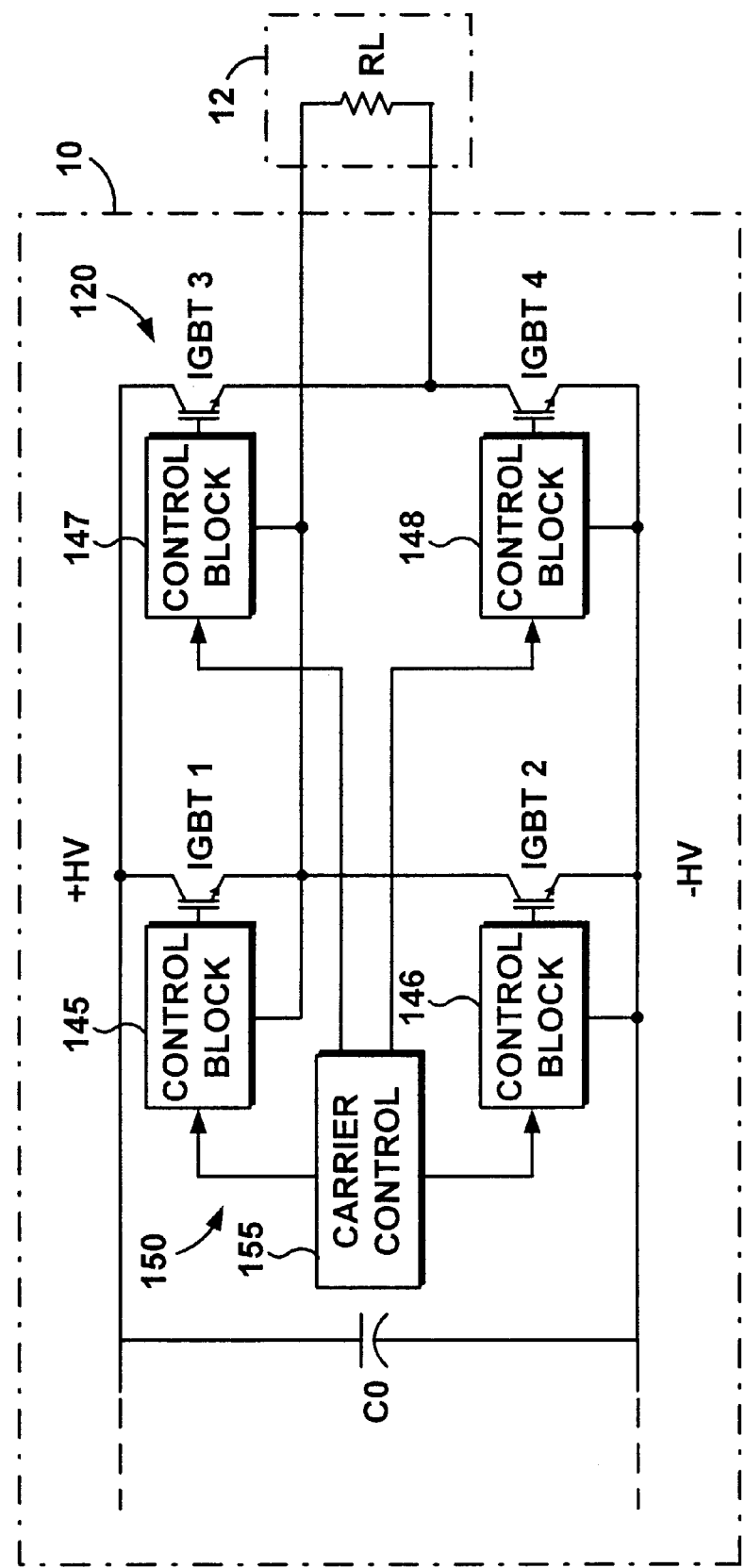
FIG. 3 is a schematic representation of a protection system of the present invention, for protecting an H-bridge of the stimulation device of FIG. 2 from high power switching activity occurring within the H-bridge and from strong external magnetic fields.

FIG. 3 illustrates an H-bridge 120 which is typically incorporated into the implantable device 10. The ICD energy storage element of the stimulation device 10 is represented by a storage capacitor C0. Though as an illustrative example the main switches (or switching elements) of the H-bridge 120 are shown as IGBTs, other switching elements, such as power MOSFETs, SCRs (silicon-controlled rectifiers), or similar elements may be used.

Typically, the main switches are triggered in pairs. For example IGBT1 and IGBT4 receive simultaneous triggers from control blocks 145 and 148, respectively. Energy is transferred to the heart 12, represented by the load, $R_L$, from the positive rail +HV and the negative rail −HV. The next trigger is applied to IGBT2 and IGBT3, transferring energy from the positive and negative rails as before, but with current flow through the load, $R_L$, in the opposite direction.

The switches or switching elements IGBT1, IGBT2, IGBT3 and IGBT4 in the H-bridge 120 are susceptible to damage and/or destruction in the event of the application of a trigger that falls outside predetermined nominal values. This includes triggers whose voltage amplitude are too large and those whose amplitudes are too small. As an example, an IGBT gate to emitter triggers with drive voltage amplitudes that exceed the nominal value may damage or destroy the gate circuit of these switches. In the event of a serious undervoltage drive at the gate of a main switch, the latter may experience damage or destruction of the switch.

A protection system 150 is added to protect the switching elements IGBT1, IGBT2, IGBT3 and IGBT4. In the example illustrated in FIG. 3, the protection system 150 generally includes four control blocks 145, 146, 147 and 148 that are connected to the switching elements IGBT1, IGBT2, IGBT3 and IGBT4, respectively, of the H-bridge 120. A carrier control circuit 155 is coupled, in turn, to the control blocks 145, 146, 147 and 148 to generate 2 MHz trains, the function of which will be explained later.

Figure 4:
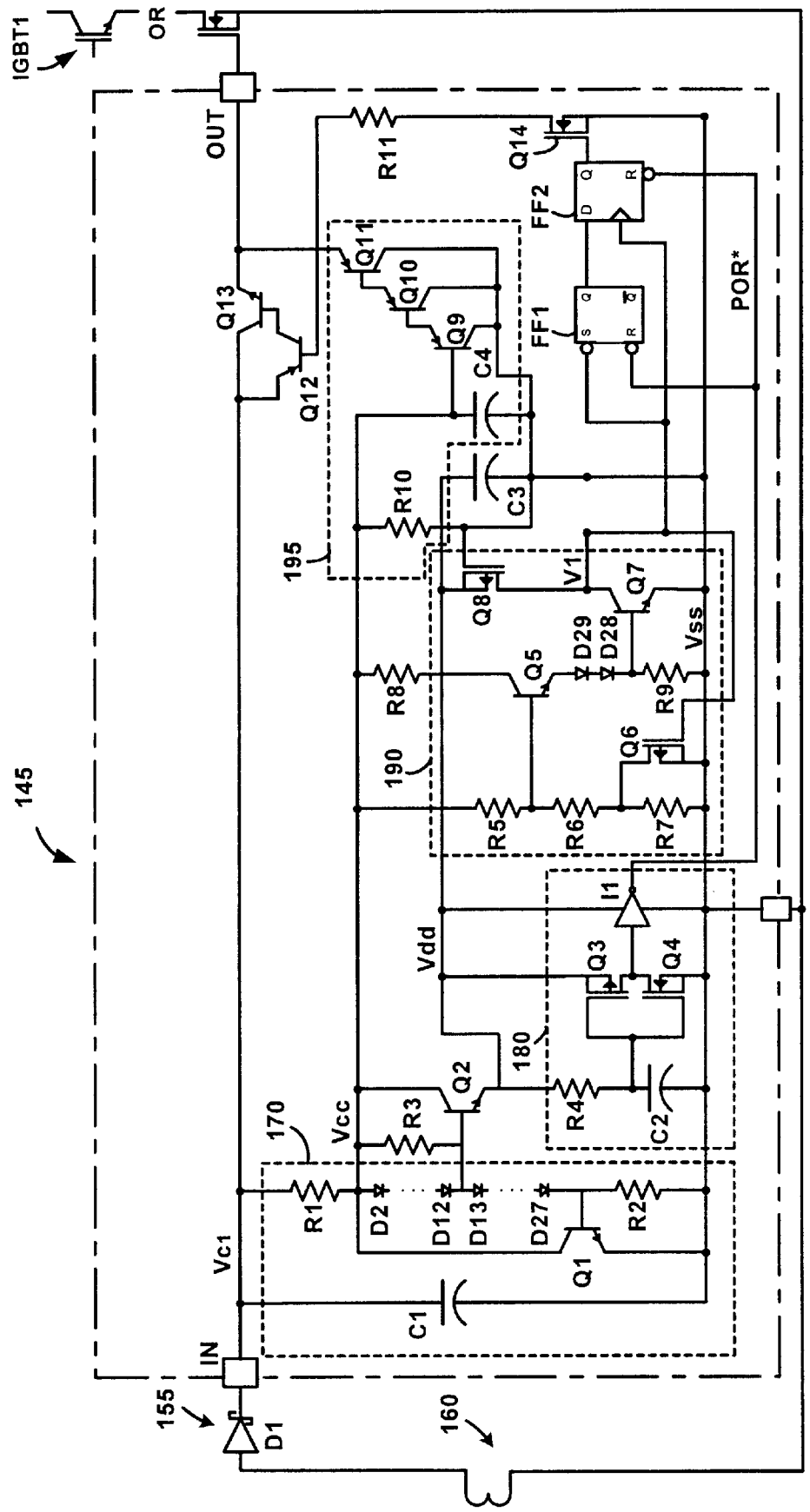
FIG. 4 is a schematic circuit diagram of the protection system of FIG. 3, shown comprised of a high frequency isolation transformer and an integrated circuit.

Referring now to FIG. 4, it illustrates a basic schematic circuit diagram of an exemplary control block, for example, the control block (or integrated circuit) 145 of FIG. 3, which is coupled to the switching element IGBT1. Part of the carrier control circuit 155 is represented in FIG. 4 by a high frequency carrier transformer 160 and a rectifying diode D1.

The carrier transformer 160 is designed to receive a 2 MHz square wave, 5V amplitude, excitation pulse train on its primary winding from a 2 MHz generator controlled by microcontroller 60. A magnetic core of the transformer 160 provides a low reluctance path for the flux between the primary and secondary windings, resulting in enhanced coupling between the transformer primary and secondary windings. The high frequency operation of the transformer 160 reduces the volume of magnetic material and allows the transformer to be readily adapted for use with the implantable stimulation device 10. The transformer secondary winding generates 18V.

The rectifier diode D1 is placed in series with the output of the secondary winding of the transformer 160, to rectify the output of transformer 160, resulting in a DC voltage on an energy storage capacitor C1 that forms part of the control block 145. The combination of the storage capacitor C1, resistors R1 and R2, a plurality of (i.e., 26) series diodes D2 through D27, and a bipolar npn transistor Q1 forms a shunt regulator 170. The shunt regulator 170 defines a voltage $V_{cc}$ from which key bias levels are attained and/or derived. In steady state, $V_{cc}$ is equal to approximately 17.5 V, the sum of 26 forward diode drops along with $V_{BE(on)}$ for the regulating transistor Q1. A bypass capacitor C4 is connected across voltage $V_{cc}$.

Figure 5:
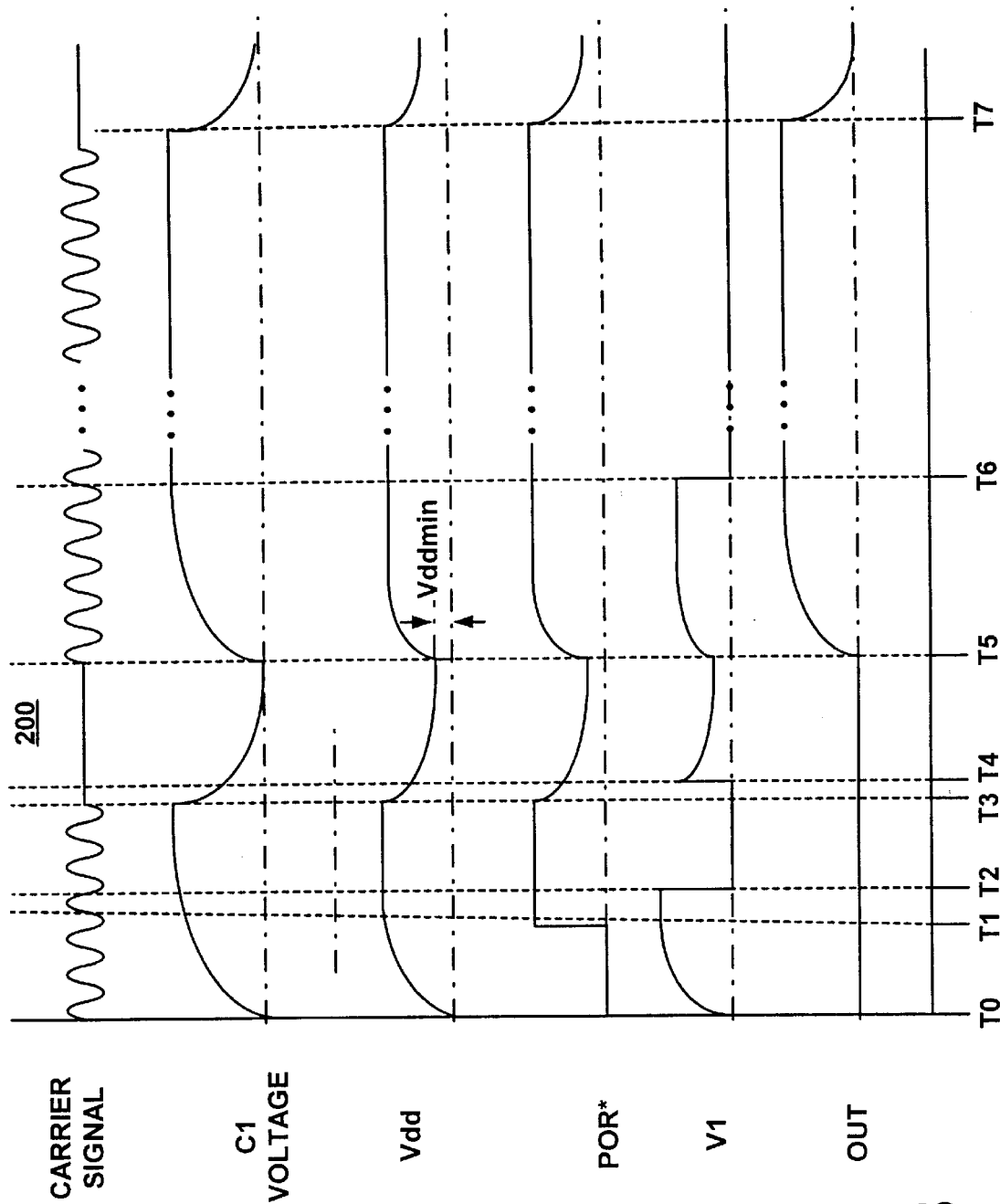
FIG. 5 is a timing diagram showing representative waveforms and relative timing at key locations within the circuit depicted in FIG. 4.

With reference to FIG. 4 and the timing diagram of FIG. 5, when a 2 MHz carrier pulse train 200 is first applied at time T0 to the primary winding of the transformer 160, an excitation appears on the secondary winding of the transformer 160, and the voltage on the capacitor C1 will increase as it is charged through the diode D1. As the voltage of capacitor C1 increases, a transistor Q2 turns on, generating a bias voltage $V_{dd}$. The bias voltage $V_{dd}$ is equal to the voltage of the transistor Q2 emitter, which, in turn, is equal to the forward voltages on the diodes D13 through D27, in addition to the Q1 base to emitter voltage, less Q2 base to emitter voltage, or the forward voltages of 15 diodes, which is approximately 0.67V. $V_{dd}$ is therefore equal to approximately 10 V in a steady-state condition. The bias voltage $V_{dd}$ acts as the supply voltage for the CMOS logic circuitry throughout the sequence of events (from T0 to T7). A bypass capacitor C3 is connected between $V_{dd}$ and $V_{ss}$.

Referring more specifically to FIG. 4, a power-on-reset (POR) circuit 180 is formed by the combination of a capacitor C2, a resistor R4, transistors Q3 and Q4 connected to form an inverter, and an inverter I1. The power-on-reset circuit 180 generates a reset signal POR* that resets a RS flip-flop FF1 and a D flip-flop FF2, ensuring that the flip-flops FF1 and FF2 are in a known and required state when the logic sequence begins. Initially, the voltage on capacitor C4 is zero, and as such, through the inverter formed by transistors Q3 and Q4 and inverter I1, the output POR* (power-on-reset bar) remains LOW or active.

The logic LOW provided by the power-on-reset circuit 180 is held for approximately 2 □s, time T1, (as defined by the RC time constant of resistor R4 and capacitor C2), after the carrier signal is initially applied to the primary winding of the transformer 160. After that period has elapsed, capacitor C4 charges to more than ½ $V_{dd}$ voltage, transistor Q4 turns ON and transistor Q3 turns OFF, dropping the input of inverter I1 to a logic LOW. The power-on-reset circuit 180 then produces a logic HIGH (POR*=HIGH) and the reset is removed from the flip-flops FF1 and FF2. POR* remains HIGH for the rest of the following sequences.

A threshold detector 190 is formed by resistors R5, R6, R7, R8, and R9, transistors Q5, Q6, Q7 and Q8, and diodes D28 and D29. The threshold detector 190 ensures that the bias voltage $V_{cc}$ has sufficient amplitude to drive IGBT1 without potential damage; otherwise the drive is inhibited. In particular, if the bias voltage $V_{cc}$ is less than 15 V, the predetermined threshold, the transistor Q5 does not receive enough base drive to switch it from its OFF state. The Q5 base voltage is determined by the divider R5, R6, R7. When this voltage is below 4 diode drops (i.e., Q5 Base to emitter, D29, D28, Q7 base to emitter), the transistor Q5 does not receive sufficient bias, and will not be able to drive transistor Q7 ON.

A pullup transistor Q8 will pull output V1 HIGH (i.e., equal to $V_{dd}$). This will not activate the flip-flop FF1 active low S input, and the flip-flop FF1 will remain reset. The voltage V1 also goes to the flip-flop FF2 clock input, which requires a LOW to HIGH transition. So, V1 being HIGH, will not clock FF2. It is only when V1 goes from LOW to HIGH, as explained later, that it will clock the flip-flop FF2 and set Q equal to the D input of the flip-flop FF2. However, the D input of the flip-flop FF2 is LOW, and thus even if the clocked output Q of the flip-flop FF2 remains LOW, this will maintain a MOSFET transistor Q14 OFF. This, in turn, will keep a Darlington pair Q12/Q13 OFF, and $V_{c1}$ will not be applied to an OUT terminal, thus preventing the signal $V_{c1}$ from propagating to IGBT1.

Conversely, when the bias voltage $V_{cc}$ exceeds the required threshold of 15V, (at time T2) transistor Q7 is turned on, and the voltage V1 drops to $V_{ss}$, a voltage very nearly equal to 0V. The input to the Set (S) line of the RS flip-flop FF1 goes LOW, producing a logic HIGH on its Q output and FF2-D input.

After approx. 4 □s (time T3 in FIG. 5), the 2 MHz train is turned OFF for approximately 2 □s until T5. During this period, voltage $V_{c1}$ applied to capacitor C1 and $V_{dd}$ applied to capacitor C3 will decay, but will not discharge to less than 3V, or Vddmin (FIG. 4). As such, the flip-flops FF1 and FF2 will maintain their state. At T4, $V_{cc}$ drops below the 15V threshold and V1 goes HIGH. This clocks the input D of the flip-flop FF2 with data equal to Q output of the flip-flop FF1. If, as explained above, $V_{cc}$ is above 15V before T3, the Q output of the flip-flop FF1 is HIGH, so that the output Q of the flip-flop FF2 will be switched HIGH.

Referring to FIG. 5, at T5, the train is reapplied and Vc1 and $V_{dd}$ will go to previous levels and V1 will remain HIGH or equal to $V_{dd}$. The flip-flop FF1 will not change state and the flip-flop FF2 will not be clocked (as V1 did not go LOW and HIGH to trigger the clock input), and therefore, the Q input of the flip-flop FF2 will remain HIGH (if prior $V_{cc}$ before T3 was above 15V). This will turn transistor Q14 ON, and causes its drain current to turn the Darlington pair (Q12, Q13) ON and Vc1 will be connected to the output "OUT" turning the IGBT (in this example IGBT1) ON. This will drive the IGBT with a sufficient driving voltage only when the transformer secondary winding generates a voltage that is sufficiently high to bring $V_{cc}$ above 15V.

The second train, starting at T5 (FIG. 5), will last for a duration of a few milliseconds necessary to deliver the high voltage shock. After this second train is turned OFF, the IGBT will be turned OFF very fast, as it will be explained further.

The introduction of transistor Q6 into comparator 190 adds a small amount of hysteresis to the comparison point by adding a small amount of positive feedback to short resistor R7. This prevents any oscillation that might otherwise occur as the voltage $V_{cc}$ traverses the threshold in either direction.

With reference to FIGS. 3 and 4, additional protection is afforded to IGBT1 by limiting the voltage that may appear at its gate while IGBT1 is OFF. While the control block 145 is OFF, without drive on its input "IN", the voltage of capacitor C4 is zero as it is discharged to $V_{ss}$ via resistor R10. Transistors Q9, Q10 and Q12, form part of a clamp circuit 195, and act as a "capacitor multiplier".

As soon as the OUT terminal voltage is equal to 3 forward diode drops (base to emitter drops of Q9, Q10 and Q11) of approximately 2V, these 3 transistors Q9, Q10 and Q11 turn ON, and act as a capacitor multiplier for C4. An equivalent capacitance between the output "OUT" and $V_{ss}$ is formed with a value of the capacitance of capacitor C4 multiplied by the Darlington current amplification by Q9, Q10 and Q11, of approximately 1000.

If the capacitance of capacitor C4 is equal to 50 pF, an equivalent capacitor of 50 nF is connected between "OUT" and $V_{ss}$. This is important to protect IGBT1 from turning ON due to transients often generated in defibrillation circuits in which they are installed. In addition, as the OUT voltage tries to exceed 2V, the conductance of 3-transistor (Q9, Q10, Q11) Darlington circuit to $V_{ss}$ goes increasingly lower, until the voltage on the OUT terminal saturates at approximately 2.2V.

Yet another feature of the control block 145 is the very fast turning OFF of IGBT1 by means of a clamp circuit 195 that includes a resistor R10 and a capacitor C4. The functionality may be understood in the following context: When IGBT is turned ON, its large gate to emitter capacitance causes the "OUT" terminal voltage to charge slower than the C4 voltage. This causes the Darlington circuit (Q9, Q10, Q11) to remain OFF.

When the carrier signal is removed to turn OFF IGBT1, the voltage on the capacitors C3 and C4 will decay faster than the voltage on the output OUT. This will bring the transistors Q9, Q10 and Q11 into conduction, thus discharging the large emitter-gate capacitance of IGBT1 across the output OUT, and ensuring that IGBT1 turns OFF very fast. The R4 conductance is multiplied by approximately 1000. If the resistor R4 is equal to 100 kOhm, an equivalent resistance of 100 Ohm or less is between OUT and $V_{ss}$. Turning the IGBT1 very fast is required to minimize its power dissipation during switching between the ON and OFF states.

Figure 6:
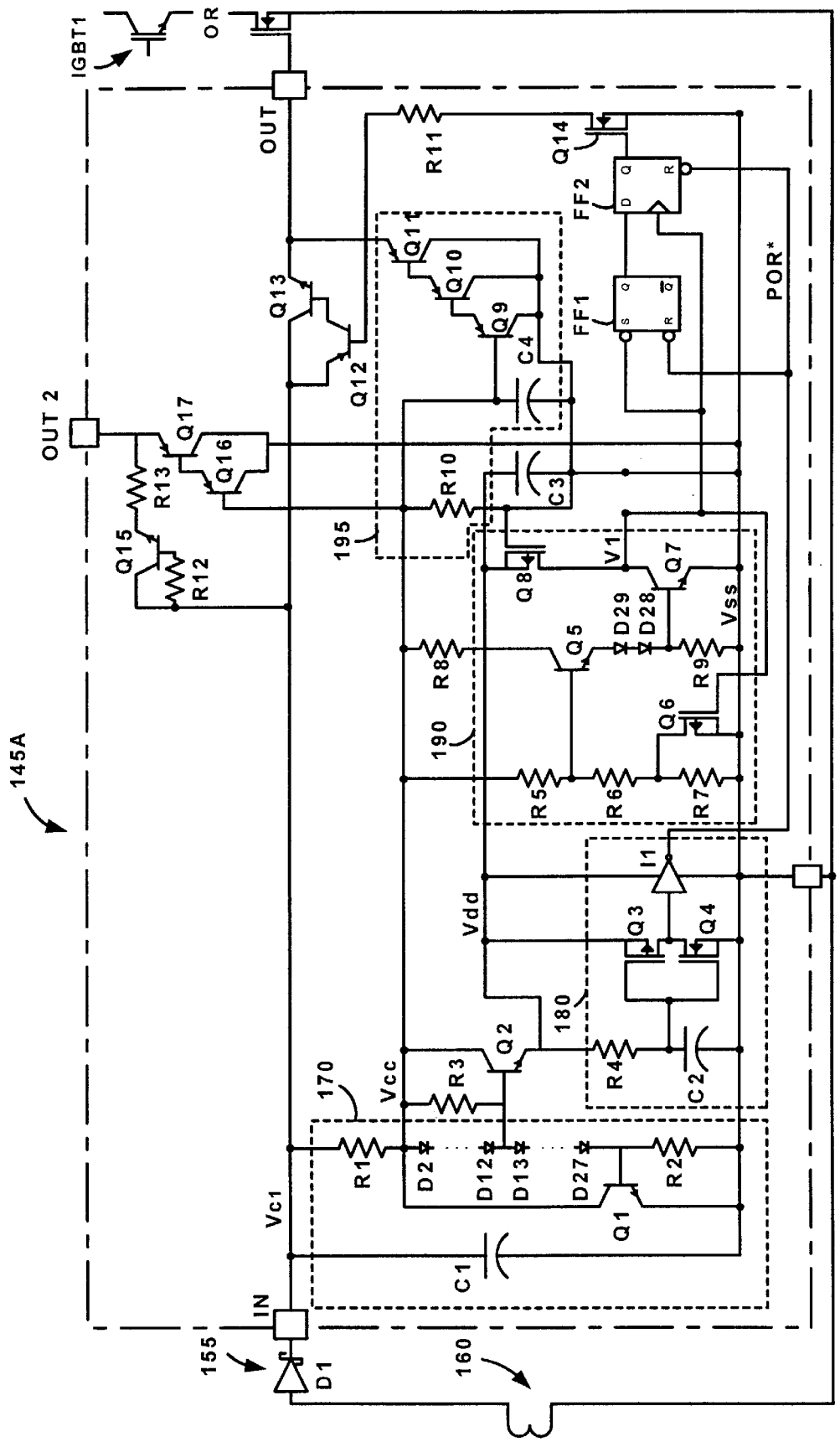
FIG. 6 is a schematic circuit diagram of another embodiment of the protection system of FIG. 3, illustrating the functionality of providing DUMP capabilities within the simulation device of FIG. 2.

Referring now to FIG. 6, it illustrates another control block 145A which is generally similar in function and design to the control block 145 of FIG. 4, but further includes a second output labeled OUT2, which may be added to the control block 145 by the inclusion of transistors Q15, Q16 and Q17, and resistors R12 and R13 with the circuit connections as shown.

The second output OUT2 of the control block 145A provides a drive for a switching element, such as IGBT2 or a MOSFET, that may, for example, be part of an implanted cardio-defibrillator (ICD) that needs to discharge one or more high voltage capacitors C0 (FIG. 3), which is referred to as DUMP function. The second output OUT2 provides such a drive irrespective of the carrier sequence, rather producing the drive voltage whenever the carrier is activated by the first train without requiring a train interruption. As shown in FIG. 6, transistor Q15 acts as a diode. When the voltage Vc1 increases, it charges the OUT2 capacitance, which is defined by the gate to emitter capacitance of IGBT1, through resistor R13. When the train stops, C4 will discharge faster than the OUT2 capacitance, and the Darlington pair (Q16, Q17) will enter conductance, discharging OUT2 to $V_{ss}$.

Normally, the output OUT2 will drive a small power MOSFET or IGBT and will require a much less driving power than the power required to drive IGBT1 through IGBT4. If only dump is required, the first train is maintained as long as required to discharge the high voltage of capacitor C0. After which, the second train is not applied, so the OUT terminal is never driven.

However, during the shock command when the sequence of the first train, pause, and the second train is applied, the output OUT2 will also be active, but this is practically acceptable. The reason is that during the shock period (i.e., a few milliseconds) while activating the output OUT, a dump circuit comprised of the IGBT in series with a resistor connected across C0 and intended to slowly discharge C0 to zero, will discharge C0 by an insignificant amount. In other terms, during the shock period, the main output OUT is activated, and the additional current through the dump circuit will be insignificant compared to the current through RL 12. As an example, if RL 12 which represents the body impedance in FIG. 3 is 50 Ohms, the dump resistance is usually 20 kOhm, or 400 times larger than RL 12, so practically only 1/400 or 0.25% of energy will be lost.

Figure 7:
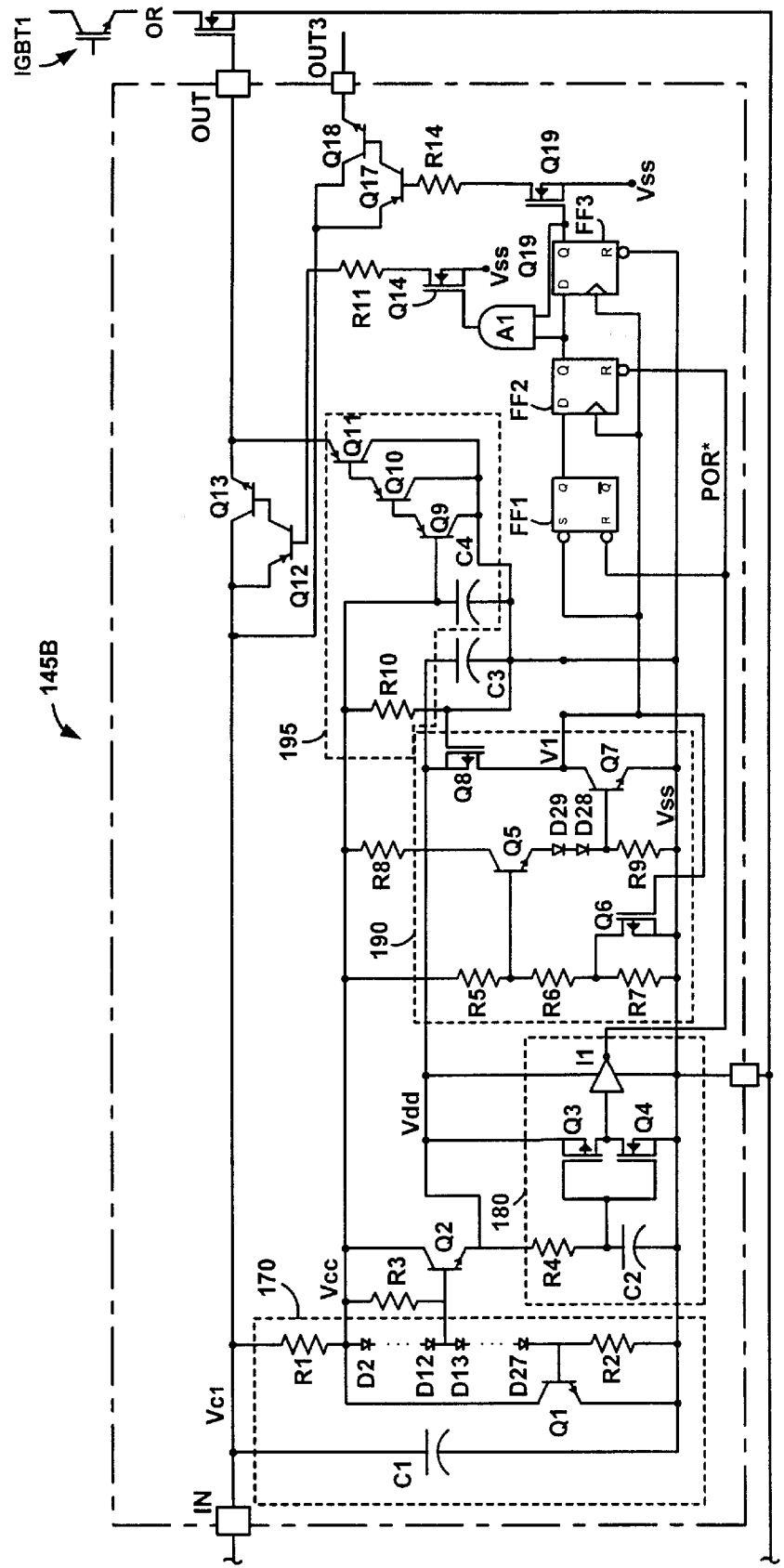
FIG. 7 is a schematic circuit diagram of still another embodiment of the protection system of FIG. 3, that includes additional logic and a second output.

Yet another embodiment of the control block 145 (FIG. 4) is illustrated in FIG. 7 and denoted by the reference numeral 145B. The control block 145B is generally similar in function and design to the control block 145 of FIG. 4, but includes additional logic in the form of a second D flip-flop FF3, an AND gate A1, a transistor Q19, a bias resistor R14, and a pair of transistors Q17, Q18. The operation of the control block 145B is similar to that of the control blocks 145 (FIG. 4) and 145A (FIG. 6) with the exception that the second output OUT3 now requires two carrier interruptions to produce an output OUT3.

The output OUT is practically unaffected by this circuit augmentation, which allows the control block 145B to control multiple outputs using carrier pulse coding, further enhancing its functionality, yet still relying on a single carrier transformer. Flip-flop FF3 will be clocked OFF (i.e., the Q output of FF3 is set to 0) at T4 (FIG. 5), as the Q output of the flip-flop FF2 is LOW, while V1 is equal to the clock signal and goes HIGH.

After the first interruption, if enough drive was applied, the AND gate A1 will receive an input HIGH from the Q output of the flip-flop FF2, and a second input which is active LOW (a bubble at this input) from the Q output of the flip-flop FF2. A HIGH output of the AND gate A1 will drive the output OUT active.

For example, if a second interruption is applied shortly after the first interruption, transistor Q13 will be turned ON during second train for a very short period, which is insufficient to charge IGBT1 on the output OUT. During this second interruption, the second D flip-flop FF3 will be switched ON (i.e., the Q output of FF3 is set to 1) by the potential V1 applied to its clock input. As shown in FIG. 5, similarly to the first interruption at time T6, V1 goes LOW–V1 will go HIGH, next LOW, and clock flip-flop FF3. As the D input of the flip-flop FF2 remains HIGH, because the output Q of the flip-flop FF1 is HIGH, the output Q of the flip-flop FF3 will go HIGH and the right active LOW AND input will go HIGH. This will make AND output LOW, thus disabling transistors Q14, Q12 and Q13, and keeping output OUT LOW. However, the Q output of the flip-flop FF3 will turn transistors Q19, Q17 and Q18 ON, applying $V_{c1}$ to the output OUT3.

While a detailed description of specific embodiments of the present invention have been provided, it would be apparent to those reasonably skilled in the field that numerous variations are possible in which the concepts and methods of the present invention may readily be applied.

What is claimed is:

1. A telemetry device for use in an implantable cardiac stimulation device including a protection device that protects the stimulation device from a potentially damaging external magnetic field, the protection device comprising:

a carrier control circuit that generates a high frequency carrier signal and that charges an energy storage device with a drive voltage;

switching elements connected to the energy storage device;

a control circuit coupled to the switching elements, that selectively inhibits the application of the drive voltage to the switching elements whenever the drive voltage falls below a predetermined threshold level, and that applies the drive voltage to the switching elements whenever a drive voltage exceeds the threshold level.

2. A device for protecting an implantable stimulation device from a potentially damaging external magnetic field, comprising:

means for generating a high frequency carrier signal and for charging an energy storage means with a drive voltage;

switching means; and control means for selectively inhibiting the application of the drive voltage to the switching elements whenever the drive voltage falls below a predetermined threshold level, and for applying the drive voltage to the switching elements whenever a drive voltage exceeds the threshold level.

3. An implantable cardiac stimulation device including a protection device that protects the stimulation device from a potentially damaging external magnetic field, the protection device comprising:

a carrier control circuit that generates a high frequency carrier signal and that charges an energy storage device with a drive voltage;

switching elements connected to the energy storage device;

a control circuit coupled to the switching elements, that selectively inhibits the application of the drive voltage to the switching elements whenever the drive voltage falls below a predetermined threshold level, and that applies the drive voltage to the switching elements whenever a drive voltage exceeds the threshold level.

4. The device according to claim 3, further including an over-voltage protection circuit that clamps a charge voltage by means of a shunt regulator circuit.

5. The device according to claim 4, further including a carrier control circuit coupled to the control block to generate 2 MHz excitation pulse train.

6. The device according to claim 5, wherein the carrier control circuit includes a high frequency carrier transformer and a rectifying diode.

7. The device according to claim 6, wherein the carrier control circuit further includes a power-on-reset circuit that generates a reset signal, and a threshold detector which ensures that a bias voltage $V_{cc}$ has sufficient amplitude to drive a switching element without potential damage, otherwise to inhibit the switching element from being driven.

8. A device for protecting an implantable stimulation device from a potentially damaging external magnetic field, comprising:

a carrier control circuit that generates a high frequency carrier signal and that charges an energy storage device with a drive voltage;

switching elements connected to the energy storage device;

a control block coupled to the switching elements, that selectively inhibits the application of the drive voltage to the switching elements whenever the drive voltage falls below a predetermined threshold level, and that applies the drive voltage to the switching elements whenever a drive voltage exceeds the threshold level.

9. The device according to claim 8, wherein the carrier signal is a 2 MHz carrier signal.

10. The device according to claim 8, further including an over-voltage protection circuit that clamps a charge voltage by means of a shunt regulator circuit.

11. The device according to claim 8, wherein the switching elements include any one or more of: an IGBT (insulated gate bipolar transistor), a power MOSFET (metal oxide semiconductor field effect transistor), or a SCR (silicon-controlled rectifier).

12. The device according to claim 8, including one control circuit for each of the switching elements.

13. The device according to claim 8, further including a carrier control circuit coupled to the control circuit to generate 2 MHz excitation pulse train.

14. The device according to claim 8, wherein the carrier control circuit further includes a power-on-reset circuit that generates a reset signal for resetting a first flip-flop FF1 and a second flip-flop FF2, ensuring that the flip-flops FF1 and FF2 are in a known and required state when a logic sequence begins.

15. The device according to claim 8, wherein the carrier control circuit further includes a threshold detector that ensures that a bias voltage $V_{cc}$ has sufficient amplitude to drive a switching element without potential damage, otherwise to inhibit the switching element from being driven.

16. The device according to claim 8, wherein the carrier control circuit includes a high frequency carrier transformer and a rectifying diode.

17. The device according to claim 16, wherein the rectifying diode is placed in series with a secondary winding of the transformer to rectify a transformer output, resulting in a DC voltage across the energy storage device.

18. The device according to claim 8, wherein the control block includes a threshold detector that determines whether the drive voltage exceeds the threshold level.

19. The device according to claim 18, wherein if the drive voltage exceeds the threshold level, the control circuit stores a corresponding level signal when an interruption of the carrier signal occurs, and upon termination of the interruption, the carrier control circuit triggers the switching element causing it to become conductive.

20. The device according to claim 19, wherein the switching element remains conductive as long as the carrier signal is applied.

21. The device according to claim 20, wherein the control circuit includes a quick discharge circuit; and wherein when the carrier signal is interrupted, the quick discharge circuit causes the conductive switching element to be discharged expeditiously.

22. The device according to claim 21, wherein the quick discharge circuit includes three transistors that are configured as a triple Darlington circuit.

23. The device according to claim 21, wherein the quick discharge circuit provides a low impedance path across the conductive switching element during discharge, rendering the switching element untriggerable, and thus protected from inadvertent triggers and high voltage transients.

* * * * *